United States Patent
Schaeffer

(10) Patent No.: US 7,670,369 B2
(45) Date of Patent: Mar. 2, 2010

(54) ENDOLUMINAL PROSTHESIS

(75) Inventor: Darin G. Schaeffer, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 529 days.

(21) Appl. No.: 11/545,290

(22) Filed: Oct. 10, 2006

(65) Prior Publication Data

US 2007/0088425 A1   Apr. 19, 2007

Related U.S. Application Data

(60) Provisional application No. 60/726,312, filed on Oct. 13, 2005.

(51) Int. Cl.
*A61F 2/06* (2006.01)
(52) U.S. Cl. .................................... 623/1.31
(58) Field of Classification Search ........ 623/1.11–1.31
See application file for complete search history.

(56) References Cited

U.S. PATENT DOCUMENTS

| | | |
|---|---|---|
| 4,604,762 A | 8/1986 | Robinson |
| 4,705,517 A | 11/1987 | DiPisa, Jr. |
| 4,728,328 A | 3/1988 | Hughes et al. |
| 4,787,899 A | 11/1988 | Lazarus |
| 4,850,999 A | 7/1989 | Planck |
| 5,064,435 A | 11/1991 | Porter |
| 5,078,726 A | 1/1992 | Kreamer |
| 5,084,065 A | 1/1992 | Weldon et al. |
| 5,123,917 A | 6/1992 | Lee |
| 5,151,105 A | 9/1992 | Kwan-Gett |
| 5,156,620 A | 10/1992 | Pigott |
| 5,163,951 A | 11/1992 | Pinchuk et al. |
| 5,211,658 A | 5/1993 | Clouse |
| 5,219,355 A | 6/1993 | Parodi et al. |
| 5,236,447 A | 8/1993 | Kubo et al. |
| 5,258,027 A | 11/1993 | Berghaus |
| 5,282,824 A | 2/1994 | Gianturco |
| 5,330,528 A | 7/1994 | Lazim |
| 5,380,328 A | 1/1995 | Morgan |
| 5,667,523 A * | 9/1997 | Bynon et al. ............... 623/1.13 |
| 5,723,003 A | 3/1998 | Winston et al. |
| 5,916,264 A | 6/1999 | Von Oepen et al. |
| 5,928,279 A | 7/1999 | Shannon et al. |
| 5,980,565 A | 11/1999 | Jayaraman |

(Continued)

FOREIGN PATENT DOCUMENTS

WO   WO 98/53761 A1   12/1998

OTHER PUBLICATIONS

International Search Report mailed Mar. 28, 2007 for International Application No. PCT/US2006/040255.

*Primary Examiner*—Suzette J Gherbi
(74) *Attorney, Agent, or Firm*—Brinks Hofer Gilson & Lione

(57) ABSTRACT

An endoluminal prosthesis is disclosed and comprises a first generally tubular stent, a second generally tubular stent, and a generally tubular graft member concentrically disposed between the first and second stents. One or more of the first and second stents may have a body portion and a flaring portion. The first and second stents each may have a recoil force such that the combined application of the first and second recoil forces secures the graft member between the first and second stents.

8 Claims, 6 Drawing Sheets

U.S. PATENT DOCUMENTS

| | | | |
|---|---|---|---|
| 6,004,348 A * | 12/1999 | Banas et al. | 623/23.7 |
| 6,086,610 A | 7/2000 | Duerig et al. | |
| 6,124,523 A * | 9/2000 | Banas et al. | 623/1.15 |
| 6,168,619 B1 | 1/2001 | Dinh et al. | |
| 6,168,620 B1 | 1/2001 | Kerr | |
| 6,214,040 B1 | 4/2001 | Jayaraman | |
| 6,245,099 B1 * | 6/2001 | Edwin et al. | 623/1.13 |
| 6,245,100 B1 | 6/2001 | Davila et al. | |
| 6,296,661 B1 | 10/2001 | Davila et al. | |
| 6,579,307 B2 | 6/2003 | Sarac | |
| 6,740,113 B2 | 5/2004 | Vrba | |
| 6,911,040 B2 | 6/2005 | Johnson et al. | |
| 6,939,369 B2 | 9/2005 | Osborne et al. | |
| 7,041,126 B2 | 5/2006 | Shin et al. | |
| 7,041,127 B2 * | 5/2006 | Ledergerber | 623/1.31 |
| 7,060,089 B2 | 6/2006 | Ley et al. | |
| RE40,122 E * | 2/2008 | Thompson | 623/1.13 |
| 7,393,357 B2 * | 7/2008 | Stelter et al. | 623/1.11 |
| 2003/0074049 A1 * | 4/2003 | Hoganson et al. | 623/1.13 |
| 2004/0054396 A1 | 3/2004 | Hartley et al. | |
| 2005/0131519 A1 | 6/2005 | Hartley | |
| 2005/0149166 A1 * | 7/2005 | Schaeffer et al. | 623/1.13 |
| 2005/0154447 A1 | 7/2005 | Goshgarian | |
| 2005/0159803 A1 | 7/2005 | Lad et al. | |
| 2005/0159804 A1 | 7/2005 | Lad et al. | |
| 2005/0171598 A1 | 8/2005 | Schaeffer | |
| 2005/0177222 A1 * | 8/2005 | Mead | 623/1.13 |
| 2005/0209679 A1 | 9/2005 | Melsheimer | |
| 2005/0222668 A1 | 10/2005 | Schaeffer et al. | |
| 2006/0058864 A1 | 3/2006 | Schaeffer et al. | |
| 2006/0122685 A1 * | 6/2006 | Bonsignore et al. | 623/1.13 |
| 2006/0287708 A1 * | 12/2006 | Ricci et al. | 623/1.15 |

* cited by examiner

ENDOLUMINAL PROSTHESIS

RELATED APPLICATIONS

This application claims the benefit of the filing date under 35 U.S.C. §119(e) of U.S. Provisional Patent Application Ser. No. 60/726,312, filed Oct. 13, 2005, which is incorporated herein by reference.

BACKGROUND OF THE INVENTION

1. Field of the Invention

This application relates to medical devices. In particular, this application relates to endoluminal devices suitable for various medical applications and the methods for making and using such endoluminal devices.

2. Description of Related Art

The functional vessels of human and animal bodies, such as blood vessels and ducts, occasionally weaken. For example, an aortic wall may weaken, resulting in an aneurysm. Upon further exposure to hemodynamic forces, such an aneurysm may rupture, resulting in internal bleeding, and often, death.

The use of an endoluminal device or prosthesis, such as a stent graft is well known in the art as an intervention for repairing weakened, aneurysmal, dissected or ruptured vessels. An endoluminal prosthesis is delivered in a radially compressed configuration using a catheter delivery system. The catheter is introduced into the lumen system and the prosthesis is delivered to the repair site intraluminally. The prosthesis is then expanded to engage the luminal wall. The prosthesis provides some or all of the functionality of the original, healthy vessel and/or preserves any remaining vascular integrity by replacing a length of the existing vessel wall that contains the site of vessel weakness or failure. Endoluminal prostheses such as stent grafts may be used for the treatment of various functional vessels, including body lumens such as the esophagus, bile duct, or blood vessels.

Examples of stent grafts that may be used for treating damaged or diseased body lumens are described in PCT Application WO 98/53761, entitled "A Prosthesis and a Method and Means of Deploying a Prosthesis," which is herein incorporated by reference.

Often times, a functional vessel may become damaged or defective at a branched location which includes a main lumen and at least one branch lumen extending from the main lumen. For example, an aneurysm may develop within the vasculature near the intersection between the abdominal aorta and branch vessels, such as the iliac, renal, celiac, and/or mesenteric arteries. Similarly, an aneurysm may develop near the intersection of the thoracic aorta and branch vessels, such as the innominate, left common carotid, and the left subclavian arteries. Repair of a damaged or defective branched vessel is particularly challenging because the stent graft must cover the entire affected area without occluding blood flow or obscuring access to adjacent lumens.

Various stent grafts have been provided for repairing main body lumens and spanning branch vessels without occluding fluid flow thereto. For example, a stent graft may be provided that has one or more fenestrations or apertures in the side wall of the stent graft. The stent graft may be deployed within a main vessel so that the fenestration is aligned with a branch vessel to allow fluid communication between the main vessel and the branch vessel.

In many cases, the vasculature is not symmetric. In addition, even with symmetrical vasculature, physiological forces may cause a previously placed stent graft to move causing the position of the fenestration to move with respect to the branch vessel. In other instances, where the disease extends into the branch vessel and affects the ostium of the branch vessel, a stent graft deployed within the main vessel may not properly seal and secure to the branch vessel and may lead to leaks (endoleaks) between the stent graft and the main vessel, reduced blood flow to the branch vessels, and/or may obscure access to portions of the branch vessel, necessitating further interventional procedures.

In cases such as these, a branch vessel prosthesis may be provided instead of or in addition to a main vessel prosthesis. For example, an abdominal aortic stent graft may be provided that extends over branch arteries such as the renal arteries, the celiac arteries, or the mesenteric arteries and that has one or more fenestrations that are alignable therewith. A branch vessel prosthesis may then be provided and attached to the abdominal aortic stent graft through a fenestration in the stent graft to complete the prosthesis.

United States Published Patent Application Nos. 2006/0058864, 2005/0222668, 2005/0171598, and 2005/0149166 A1 disclose various systems for repairing branched vessels, the disclosures of which are incorporated by reference here. Various aspects of each of these disclosures may be used in conjunction with the present invention.

Presently, the manufacture of stent grafts or covered stents requires specialized secondary procedures or specialized stent-attachment mechanisms. For example, the stent may be attached to a graft using external components such as hooks, sutures or other fasteners. Alternatively, a covered stent may be formed by using a dip-coating process to apply the graft to the stent. Such components and processes are both labor-intensive and costly.

Thus, there is a need for an endoluminal prosthesis that includes a stent and a graft where the stent and graft are secured together without the use of such attachment procedures or mechanisms.

SUMMARY

An endoluminal prosthesis having a compressed configuration and an expanded configuration is provided and includes a first generally tubular stent, a second generally tubular stent, and a generally tubular graft member arranged substantially concentrically. For example, the second stent may be disposed radially about the first tubular stent and the tubular graft member may be disposed between the first and second stents. The first stent may have a first recoil force and the second stent may have a second recoil force such that the combined application of the first and second recoil forces secures the graft member between the first and second stents. This may be without the need for suturing, gluing or otherwise adhering the stents to the graft material. Accordingly, the stents and the graft form inseparable layers.

The first stent may include a flaring portion and a body portion. In the compressed configuration, the flaring portion and the body portion lie in the same plane. In one example, the flaring portion of the first stent extends longitudinally beyond an end of the second stent in the compressed configuration. In the expanded configuration, the body portion may be substantially parallel to an axis of the prosthesis, while the flaring portion flares radially outwardly from the axis. In other examples, the second stent comprises a flaring portion and a body portion. In further examples, each of the first and second stents includes a flaring portion and a body portion. In these examples, the respective flaring portions and body portions may be concentrically aligned. The prosthesis may have one or more flaring portions as necessary, for example, a flaring portion at each end.

The recoil force of the second stent may be greater than the recoil force of the first stent. When the stent graft is expanded, the combined application of the first and second recoil forces secures the graft member between the first and second stents. The recoil force may be expressed in terms of the reduction in diameter of the stent from an expanded configuration. The recoil force of the first stent may be between about 0% and about 7%. Accordingly, the first recoil force decreases the diameter of the first stent by about 0% to about 7%. The recoil force of the second stent may be between about 4% and about 10% so that the second recoil force decreases the diameter of the second stent by about 4% to about 10%.

The first stent and the second stent each may be balloon-expandable, self-expanding, or both. One of the first and second stents may be self-expanding while the other may be balloon-expandable. In some examples, at least one of the first and second stents comprises a series of stent rings.

Stents may be made from any suitable biocompatible material, including, but not limited to, materials selected from the group of stainless steel, platinum, gold, titanium, Nitinol, nickel-titanium alloys, MP35N, nickel-cobalt alloys, Cobalt L-605, cobalt-chromium alloys, biocompatible metals, metal-alloys and polymeric materials.

A system for repairing a branched vessel having a main lumen and a branch lumen also is provided and comprises a main vessel stent graft and a branch vessel stent graft. The main vessel stent graft may have a fenestration and is deployable within the main lumen so that the fenestration is aligned with the branch lumen. The branch vessel stent graft may have a body portion and a flaring portion and is deployable within the branch lumen so that the flaring portion extends at least partially through the fenestration of the main vessel stent graft. The main vessel stent graft and/or the branch vessel stent graft may include any of the features of an endoluminal prosthesis described above.

BRIEF DESCRIPTION OF THE DRAWINGS

The invention may be better understood with reference to the following drawings and description. The components in the figures are not necessarily to scale. The emphasis is placed upon illustrating the principles of the invention. Furthermore, reference numerals are provided to identify corresponding parts maintained throughout the different views.

DETAILED DESCRIPTION OF PREFERRED EMBODIMENTS OF THE INVENTION

Throughout this specification and in the appended claims, the terms "distal" and "distally" are intended to refer to a location or direction that is, or a portion of a device that when implanted is further downstream in the direction of or with respect to blood flow. The terms "proximal" and "proximally" are intended to refer to a location or direction that is, or a portion of a device that when implanted is further upstream in the direction of or with respect to blood flow.

The term "prosthesis" means any replacement for a body part or function of that body part. It may also mean a device that enhances or adds functionality to a physiological system.

The term "stent" means any device or structure that adds rigidity, expansion force or support to a body part, for example, a diseased, damaged, or otherwise compromised body lumen.

The term "graft" describes an object, device, or structure that is joined to or that is capable of being joined to a body part to enhance, repair, or replace a portion or a function of that body part. Grafts that may be used to repair body vessels include, for example, films, coatings, or sheets of material that are formed or adapted to conform to the body vessel that is being enhanced, repaired, or replaced. A stent may be attached to a graft to form a "stent graft."

A stent may be self-expanding, balloon-expandable or may have characteristics of both. An example of a type of stent is a so-called zigzag stent that has alternating struts and peaks (i.e. bends) and defines a substantially cylindrical space. A variety of other stent configurations are also contemplated by the use of the term "stent."

The term "endoluminal" describes objects that are found or may be placed inside a lumen in the human or animal body. A "lumen" is a cavity, channel, or space that is found within a vessel. In the human or animal body, there are both existing or natural lumens and lumens created by surgical intervention. Typical existing lumens include those found in blood vessels, parts of the gastrointestinal tract, ducts such as bile ducts, parts of the respiratory system, etc. An "endoluminal prosthesis" is thus a prosthesis that is found or that may be placed inside a lumen. Stents, grafts, and stent grafts are examples of types of endoluminal prostheses.

The term "flaring" encompasses all forms of the term "flare," including, but not limited to the terms "flared" and "flareable."

Figure 1:
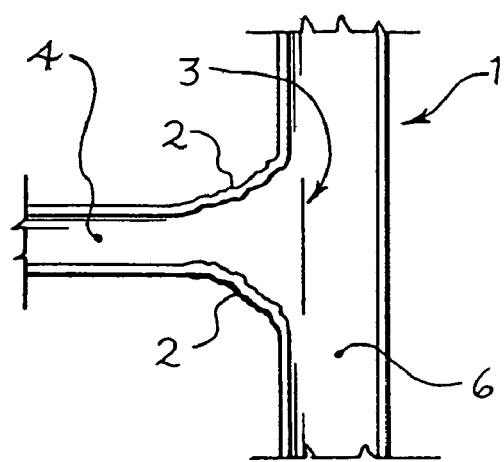
FIG. 1 is a partial, cross-sectional view of a damaged or defective branched vessel.

FIGS. 1-4 are provided as background and illustrate exemplary uses for stent grafts. FIG. 1 shows a partial cross-sectional view of a diseased branched body vessel 1. The body vessel includes a main vessel portion 6 and a branch vessel portion 4 that extends therefrom. An aneurysm 2 is formed in the ostium 3 of the branch vessel 4. The ostium 3 is generally perpendicular to the main vessel 6 of the branched body vessel 1. If such an aneurysm is left untreated, the vessel 1 may become further weakened and may rupture. The branched body vessel shown in FIG. 1 may be repaired by one or more stents and/or stent grafts disclosed here.

Figure 2:
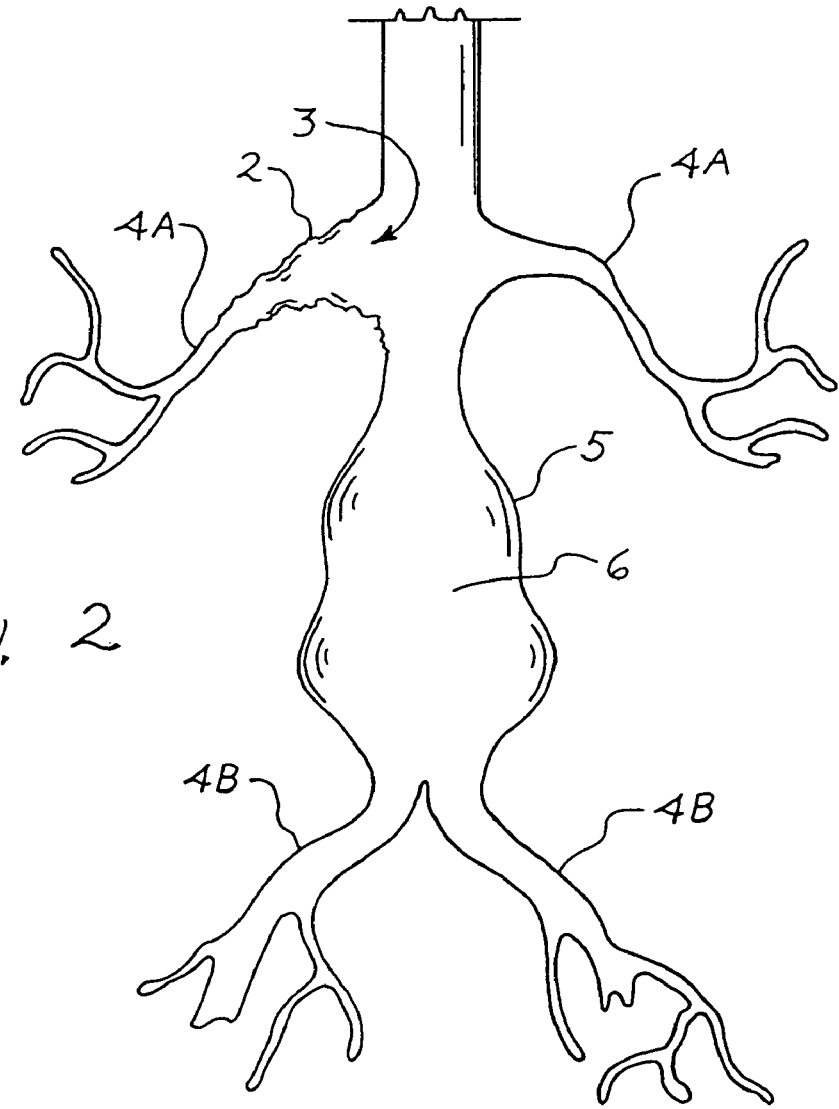
FIG. 2 is a partial, cross-sectional view of an abdominal aortic aneurysm extending into the renal arteries.

FIG. 2 shows a partial cross-sectional view of another diseased body vessel that includes a main branch 6, the aorta, and various branch vessels, such as the renal arteries 4A and the iliac arteries 4B. An abdominal aortic aneurysm 5 has formed and extends from the iliac arteries 4B proximally to a location just distal of the renal arteries 4A. In addition, an aneurysm 2 is formed in the ostium 3 of one of the renal arteries 4A. As with the diseased vessel shown in FIG. 1, the abdominal aortic aneurysm shown in FIG. 2 may be repaired by one or more stents and/or stent grafts disclosed here.

Figure 3:
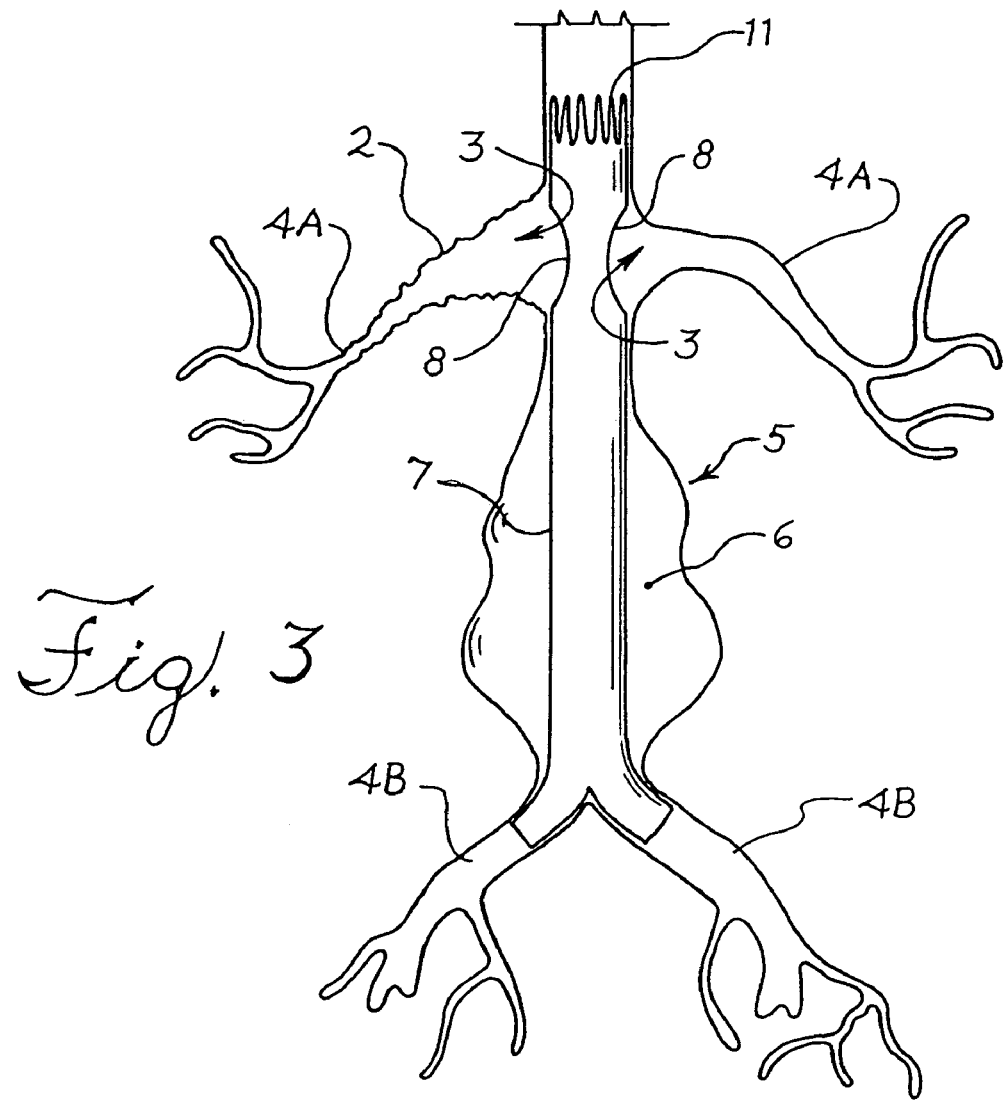
FIG. 3 is a partial, cross-sectional view of an abdominal aortic aneurysm extending into the renal arteries, showing a fenestrated stent graft placed in the aorta such that fenestrations are aligned with the renal arteries.

In FIG. 3, a tubular stent graft 7 has been placed within the aorta 6 so that its proximal end is positioned proximally of the renal arteries 4A. An anchoring device 11, such as a bare wire stent, is provided and is configured to engage healthy tissue in the aorta 6 and to provide support for the stent graft 7 to prevent longitudinal movement that may be caused by pulsatile blood flow. The stent graft 7 extends distally towards the iliac arteries 4B where it bifurcates and divides blood flow between the two iliac branches. The stent graft 7 seals against the aorta proximally and distally of the abdominal aortic aneurysm 5, thereby preventing blood flow to the aneurysm 5.

The stent graft 7 shown in FIG. 3 has a plurality of holes or fenestrations 8 that are positioned in alignment with the renal arteries 4A. The fenestrations 8 allow blood to flow to the renal arteries 4A and prevent blockage or occlusion that, if untreated, could cause narrowing of the renal arteries and could cause renal failure.

Figure 4:
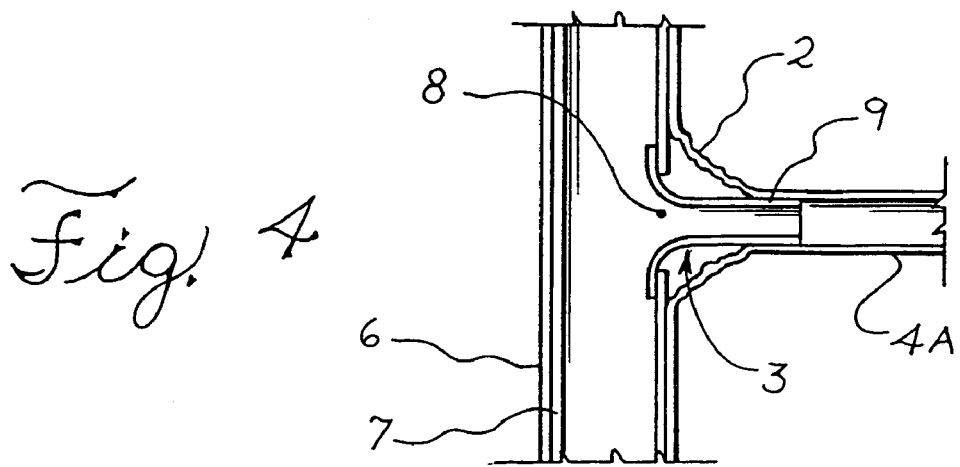
FIG. 4 is a partial, cross-sectional view of a damaged or defective branched vessel, showing a fenestrated stent graft placed in the main lumen such that a fenestration aligns with a branch lumen and a flareable stent graft is placed in the branch lumen and through the fenestration.
Figure 4A:
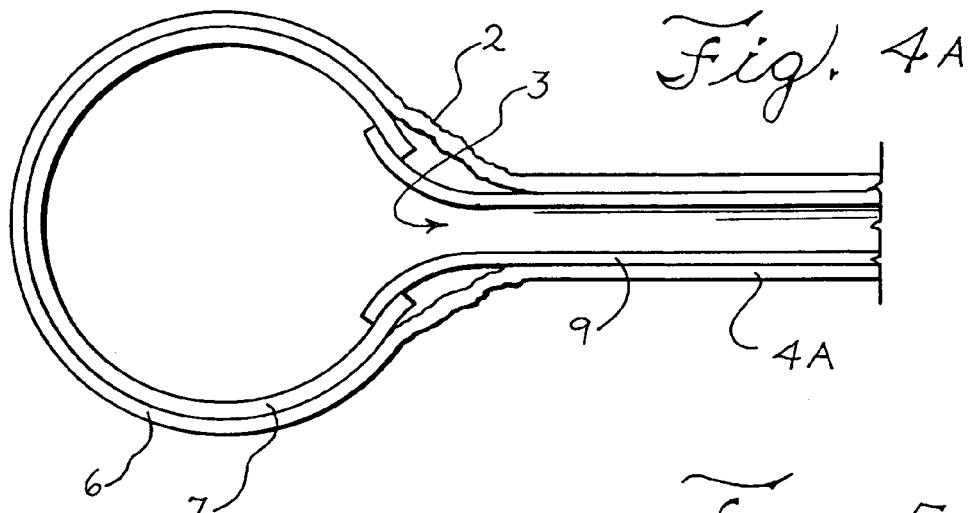
FIG. 4A is a cross-sectional top view of the fenestrated stent graft and flareable stent graft deployed in the branched vessel shown in FIG. 4.

As shown FIGS. 4 and 4A, a second stent graft 9 may be provided to repair or exclude the aneurysm 2 in the ostium 3 of the renal artery 4A. The branch vessel stent graft 9 extends proximally through the fenestration 8 of the fenestrated stent graft 7 and distally into the renal artery 4A. The distal end of the stent graft 9 is secured within a healthy portion of the renal artery 4A and the proximal end of the stent graft 9 is secured to the fenestrated stent graft 7. Securement of the branch stent graft 9 to the fenestrated stent graft 7 may be facilitated by flaring the proximal end of the branch stent graft 9 so that it engages the fenestration, as shown in FIGS. 4 and 4A. The branch vessel stent graft 9 seals against the fenestration 8 in the main stent graft 7 and prevents blood flow to the aneurysm 2.

Figure 8:
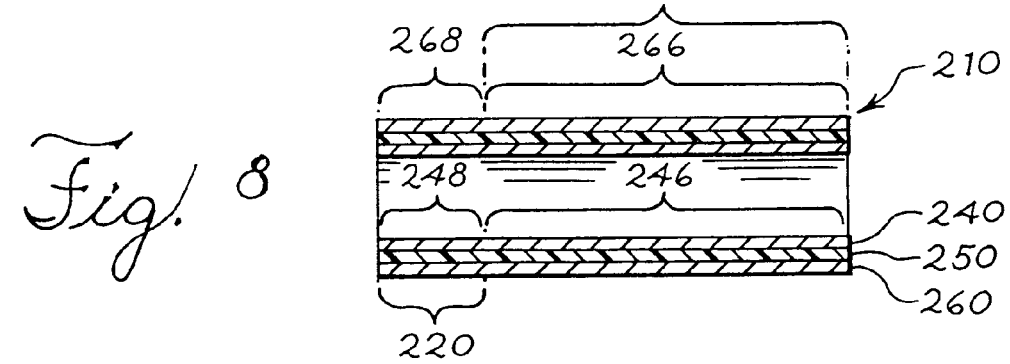
Figure 9:
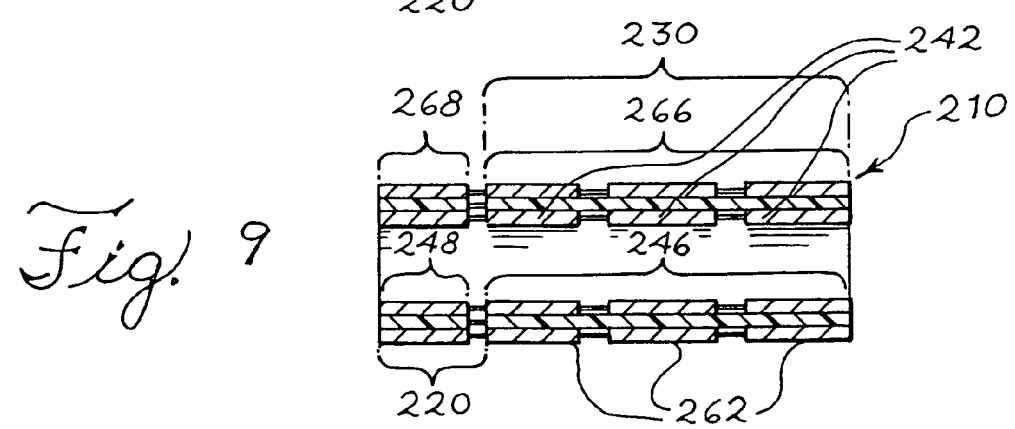
Figure 10:
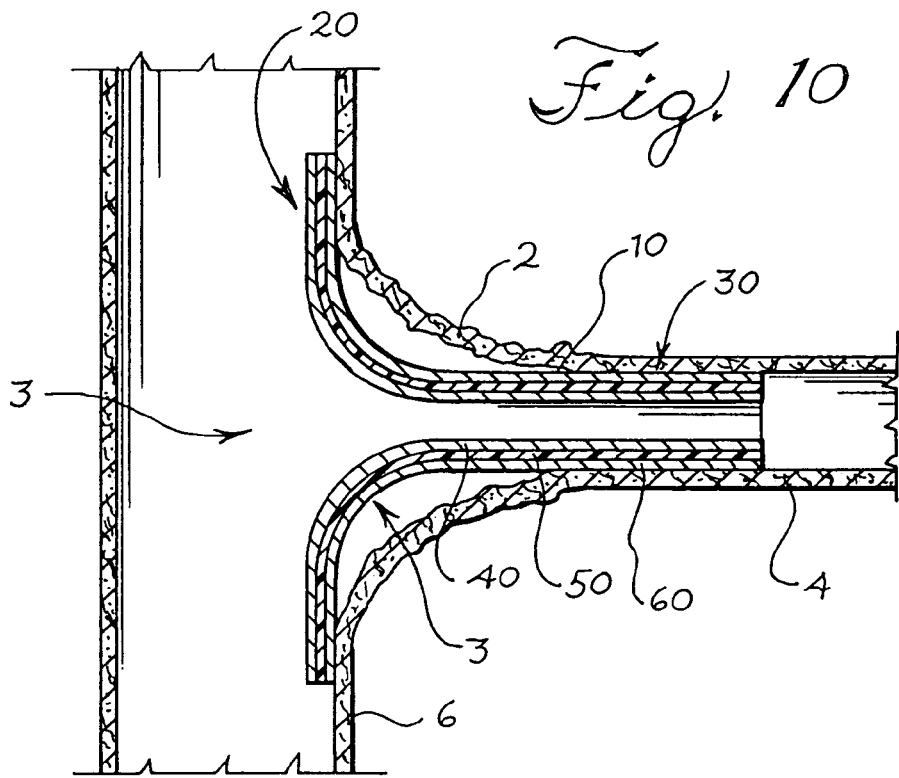
FIG. 10 is a schematic, cross-sectional view of the flareable stent graft of FIG. 8 deployed within the ostium of a branch lumen.
Figure 11:
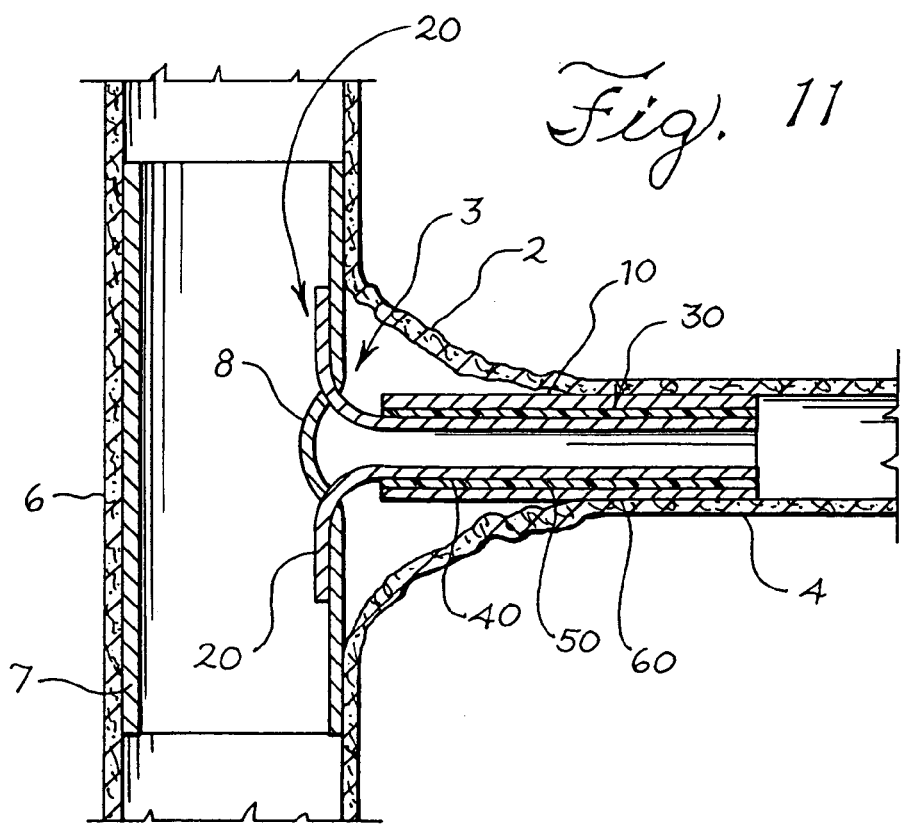
FIG. 11 is a schematic, cross-sectional view of the flareable stent graft of FIG. 6 deployed within a fenestration of a fenestrated stent graft.

FIGS. 5 through 11 illustrate various exemplary configurations of stent graft prostheses 10. Although the figures illustrate flareable stent grafts, it may be understood that non-flaring stent grafts are contemplated. The grafts 10 may be used independently, as shown in FIG. 10. Alternatively, the grafts 10 may be used in conjunction with a fenestrated stent graft, as shown in FIG. 11.

Figure 5:
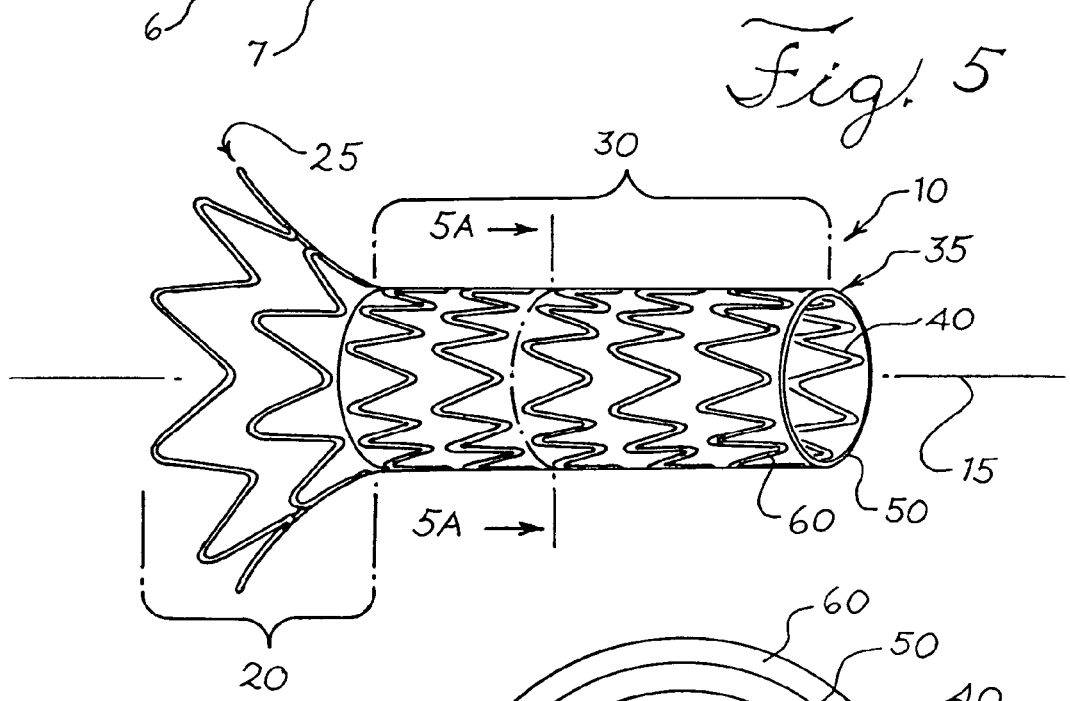
FIG. 5 is a perspective view of a flareable stent graft.

FIG. 5 shows a flareable stent graft 10 in an expanded configuration. The stent has a proximal end 25, a distal end 35, and a longitudinal axis 15 extending therethrough. The stent graft 10 may be tubular and may have flaring portion 20 and a body portion 30. In the expanded configuration, the body portion 30 may be generally cylindrical while the flaring portion 20 may be flared radially outwardly with respect to the longitudinal axis 15. When the stent graft 10 is to be used in conjunction with a fenestrated stent graft, at least a part of the flaring portion 20 may have a diameter that is greater than the diameter of the fenestration.

FIGS. 6-9 show various flareable stent grafts 10 in a compressed configuration. In the compressed configuration, the generally tubular body portion 30 and flaring portion 20 are unexpanded and the flaring portion 20 may lie in the same plane as the body portion 30, substantially parallel to the longitudinal axis 15.

Figure 5A:
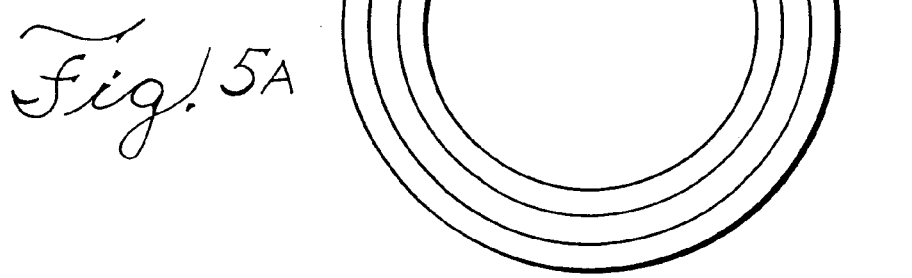
FIG. 5A is a schematic cross-sectional end-view of a stent graft.

FIG. 5A shows a transverse cross-section of a stent graft. The stent graft 10 comprises a first inner tubular stent 40 and a second outer tubular stent 60. The inner stent 40 may be disposed concentrically within the outer stent 60. A generally tubular graft member 50 may be disposed between the inner and outer stents 40, 60 and may be retained therebetween. The inner and outer stents 40, 60 may have different lengths or may have substantially the same length. The graft member 50 may have a different length or may have substantially the same length as either the inner or outer stent 40, 60.

Various graft materials are contemplated for graft member 50 and include any suitable biocompatible material. The material of the graft member 50 may be formed from a biocompatible woven or non-woven fabric or other material. For example, the material may be woven polyester having a twill weave and a porosity of about 350 ml/min/cm$^2$ (available from VASCUTEK® Ltd., Renfrewshire, Scotland, UK), although other configurations are contemplated.

Graft materials may include porous sheets containing a biocompatible polymer. Examples of biocompatible polymers from which porous sheets may be formed include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible.

Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet may be used to make a graft material, provided the final porous material is biocompatible. Polymers that may be formed into a porous sheet include polyolefins, polyacrylonitrile, nylons, polyaramids and polysulfones, in addition to polyesters, fluorinated polymers, polysiloxanes and polyurethanes as listed above. The porous sheet may be made of one or more polymers that do not require treatment or modification to be biocompatible.

The graft material also may include a biocompatible polyurethane. Examples of biocompatible polyurethanes include THORALON (THORATEC, Pleasanton, Calif.), BIOSPAN, BIONATE, ELASTHANE, PURSIL and CARBOSIL (POLYMER TECHNOLOGY GROUP, Berkeley, Calif.). As described in U.S. patent application Publication Ser. No. 2002/0065552 A1, incorporated herein by reference, THORALON is a polyetherurethane urea blended with a siloxane-containing surface modifying additive. Specifically, the polymer is a mixture of base polymer BPS-215 and an additive SMA-300.

The concentration of additive may be in the range of 0.5% to 5% by weight of the base polymer. The BPS-215 component (THORATEC) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). The SMA-300 component (THORATEC) is a polyurethane comprising polydimethylsiloxane as a soft segment and the reaction product of MDI and 1,4-butanediol as a hard segment. A process for synthesizing SMA-300 is described, for example, in U.S. Pat. Nos. 4,861,830 and 4,675,361, which are incorporated herein by reference. A porous polymeric sheet may be formed from these two components by dissolving the base polymer and additive in a solvent such as dimethylacetamide (DMAC) and solidifying the mixture by solvent casting or by coagulation in a liquid that is a non-solvent for the base polymer and additive.

Alternatively, naturally occurring biomaterials, such as collagen, may be highly desirable, particularly a specially derived collagen material known as an extracellular matrix (ECM), such as small intestine submucosa (SIS®). Besides SIS, examples of ECM's include pericardium, stomach submucosa, liver basement membrane, urinary bladder submucosa, tissue mucosa and dura matter. SIS® is particularly useful, and may be made in the fashion described in Badylak et al., U.S. Pat. No. 4,902,508; Intestinal Collagen Layer described in U.S. Pat. No. 5,733,337 to Carr and in 17 Nature Biotechnology 1083 (November 1999); Cook et al., PCT Application WO 98/22158, dated 28 May 1998 which is the published application of PCT/US97/14855, each of which is incorporated herein by reference. Irrespective of the origin of the material (synthetic versus naturally occurring), the material may be made thicker by making multilaminate constructs, for example SIS® constructs as described in U.S. Pat. Nos. 5,968,096; 5,955,110; 5,885,619; and 5,711,969, each of which is incorporated herein by reference.

In addition to xenogenic biomaterials, such as SIS®, autologous tissue may be harvested as well. Additionally, Elastin or Elastin-Like Polypeptides (ELPs) and the like offer potential as a material to fabricate the covering or frame to form a device with exceptional biocompatibility. Another alternative would be to use allographs such as harvested native valve tissue. Such tissue is commercially available in a cryopreserved state. SIS® is available form Cook Biotech, West Lafayefte, Ind., USA.

Various stent types and stent constructions may be used in a flareable stent graft 10. In general, the stents may be formed from any material and have any structure that is expandable and has sufficient radial strength to retain its shape. Suitable stent materials include, but are not limited to, stainless steel, platinum, gold, titanium, Nitinol™ and other nickel-titanium alloys, MP35N® and other nickel-cobalt alloys, Cobalt L-605™ and other cobalt-chromium alloys, other biocompatible metals, metal-alloys, as well as polymers.

Stents may be balloon-expandable or self-expanding. The stents may be radially contractible, radially distensible and/or deformable. Self-expanding stents include those that have a spring-like action which causes the stent to radially expand, or stents which expand due to the memory properties of the stent material for a particular configuration at a certain temperature. An exemplary self-expanding stent is the Z-STENT®, available from Cook Incorporated, Bloomington, Ind. USA.

In addition, stents that may be used include those described in U.S. Pat. Nos. 5,718,713; 5,741,327; 5,746,691; 5,843,175; 5,868,782; 6,042,606; 6,299,635; 6,786,922; and in U.S. Application Ser. No. 60/518,565, filed Nov. 8, 2003, each of which is incorporated herein by reference.

Each stent may have a recoil force that may be expressed in terms of the percentage of recoil that is observed in the stent (by percentage of stent diameter.) For example, a stent that is expanded to an initial diameter of 1 cm and subsequently recoils to a 0.9 cm diameter may have recoil force of 10%. A stent that is expanded to an initial diameter of 1 cm and does not recoil may have a recoil force of 0%. A stent that is expanded to an initial diameter of 1 cm and subsequently expands to a 1.1 cm diameter (for example, a self-expanding stent) may have a recoil force of approximately −10%. The recoil force of a stent may be controlled by various factors, including the use of specified raw materials to provide a predetermined recoil. Balloon-expandable stents may, in general, exhibit greater recoil than self-expanding stents. In addition, recoil is affected by the amount of cold-work that a stent receives. In general, the more a material is cold-worked, the greater the recoil force may be in a stent made from that material.

Inner and outer stents 40, 60 may be selected such that the inner stent 40, graft member 50 and outer stent 60 form inseparable layers. More particularly, inner stent 40 comprises a first recoil force and outer stent 60 comprises a second recoil force. The second recoil force may be greater than the first recoil force such that, upon expansion, the outer stent 60 retains both the graft member 50 and the inner stent 40 to form the inseparable layers of the stent graft 10. The stents 40, 60 act in concert via the combined application of the relative recoil forces to secure the graft member 50 between the inner and outer stents 40, 60, without the need for additional fasteners such as sutures or adhesives. The stents 40, 60 act in concert via the application of the relative recoil forces to secure the prosthesis in the branch vessel after deployment. Thus, the need for other means of securement, such as adhesives and sutures, may be reduced or eliminated. In one example, the inner stent 40 may have a recoil force of about 0% to about 7% and the outer stent 60 may have a recoil force of about 4% to about 10%. For example, the outer stent may have a recoil force of approximately 7% and the inner stent may have a recoil force of approximately 3%.

The inner and outer stents 40, 60 each may be balloon-expandable, or they may each be self-expanding. Alternatively, one of the inner stent 40 and the outer stent 60 may be balloon-expandable and the other of the outer stent 60 and inner stent 40 may be self-expanding. For example, the outer stent may be balloon-expandable and have a recoil force of approximately 5% and the inner stent may be self-expanding and have a recoil force of approximately 4% or less.

Figure 6:
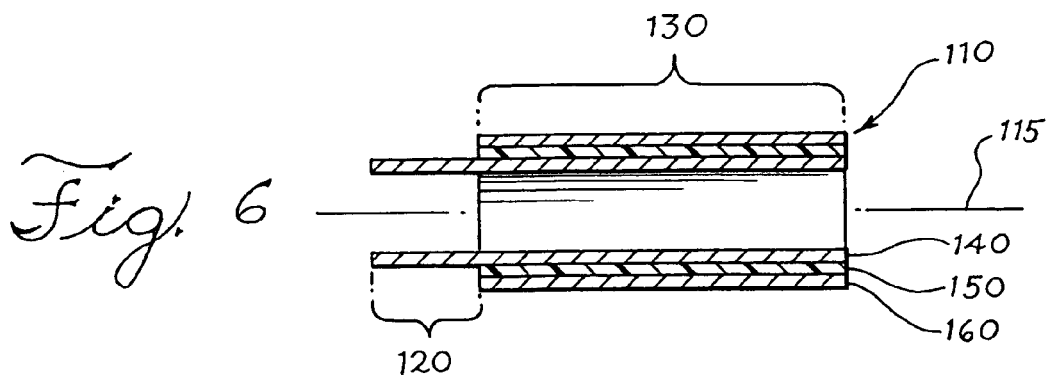
FIGS. 6-9 are schematic, cross sectional views of various flareable stent grafts.

FIG. 6 illustrates a stent graft 110 shown in a compressed configuration. The stent graft 110 may have a flaring portion 120 and a body portion 130. The body portion 130 comprises an inner stent portion 140, an outer stent portion 160, and a graft member 150 disposed therebetween. The outer stent portion 160 and graft member 150 have substantially the same length and are substantially coextensive along the longitudinal axis 115 of the stent graft 110. The inner stent portion 140 is longer than the outer stent portion 160 and graft member 150 and includes flaring portion 120. The flaring portion 120 may be coupled to and extend from the inner stent portion 140. In one example, the flaring portion 120 and the inner stent portion 140 comprise separate stents that may be joined together to form a combined stent structure. In another example, the flaring portion 120 and the inner stent portion 140 comprise portions of a unitary stent structure. In another example, the stent graft 110 may have flaring portion 120 coupled to and extending from the outer stent portion. In yet another example, the graft member covers the flaring portion 120.

The outer stent portion 160 may have a recoil force that is greater than the recoil force of the inner stent portion 140. Accordingly, when the stent graft 110 is expanded, the outer stent portion 160 may retain both the graft member 150 and the inner stent 140 to form inseparable layers of the stent graft 110.

In the compressed configuration, the flaring portion 120 and the body portion 130 are unexpanded and both the flaring portion 120 and the body portion 130 are substantially parallel relative to the longitudinal axis 115 of the stent graft 110. In the deployed configuration, the flaring portion 120 and the body portion 130 portion are expanded so that the body portion 130 is substantially parallel relative to the longitudinal axis 115 while the flaring portion 120 is at least partially flared relative to the longitudinal axis 115 (as shown in FIG. 5). Any angle of flare is contemplated and the degree of flare may be selected based on the intended application. More specifically, the flaring angle of the flaring portion 120 may vary depending on the angulation of the branch vessel with the main lumen.

Figure 7:
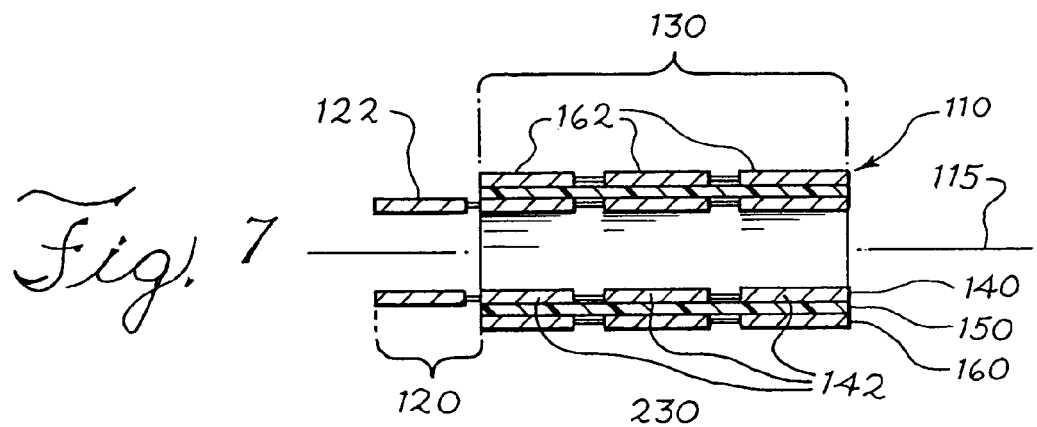

FIG. 7 illustrates another stent graft 110 that is similar to the stent graft shown in FIG. 6. The stent graft 110 may have a flaring portion 120 and a body portion 130. The body portion 130 comprises a plurality of inner stent rings 142 that may be longitudinally interconnected to form an inner stent structure 140 and a plurality of outer stent rings 162 that may be longitudinally interconnected to form an outer stent structure 160. A generally tubular graft member 150 is disposed between the inner and outer stent structures 140,160. The flaring portion 120 comprises a flaring stent ring 122 that is coupled to and extends from the inner stent portion 140.

In the example shown in FIG. 8, a stent graft 210 is shown that includes a flaring portion 220 and a body portion 230. The stent graft 210 comprises an inner stent 240, an outer stent 260, and a graft member 250. The inner stent 240, the outer stent 260, and the graft member 250 have substantially the same length. The inner stent 240 comprises an inner stent body portion 246 and an inner stent flaring portion 248, and the outer stent 260 comprises an outer stent body portion 266 and an outer stent flaring portion 268. The graft member 250 covers the body portion 230 and the flaring portion 220 of the stent graft 210. The outer stent 260 and the inner stent 240 have recoil forces that cooperate to hold the graft member 250 therebetween.

FIG. 9 illustrates a stent graft similar to the one shown in FIG. 8, except that the inner stent 240 comprises a plurality of longitudinally interconnected inner stent rings 242 and the outer stent 260 comprises a plurality of longitudinally interconnected outer stent rings 268. The flaring portion 220 comprises an outer flaring stent portion 268 and an inner flaring stent portion 248 that are coupled to and extended from the outer stent 260 and the inner stent 240 respectively In the examples shown in FIGS. 8 and 9, the outer flaring stent 268 may be generally aligned with the inner flaring stent 248 in both the compressed configuration and in the expanded or deployed configuration. Likewise, the outer stent body portion 266 is generally aligned with the inner stent body portion 246 in both the compressed configuration and the deployed configuration. The angle of the flare of the flaring portion 220 and the degree of flare may be selected based on the intended application.

Although not specifically shown, it is also contemplated that a stent graft may have multiple flaring portions. For example, a stent graft may include a first flaring portion at the proximal end and a second flaring portion at the distal end.

It is also contemplated that more than one outer stent may be positioned about at least a portion of an inner stent. For example, a first outer stent may be positioned about at least a portion of the inner stent flaring portion proximal end and a second outer stent may be positioned about at least a portion of the inner stent body portion. Alternatively, multiple outer stents may be positioned about at least a portion of the inner stent flaring portion or the inner stent tubular body portion. The multiple outer stents may be positioned adjacent to, or spaced apart from, each other.

FIGS. 10 and 11 illustrate several uses for a flareable stent graft 10. To achieve the desired result of completely repairing a branch lumen without occluding flow or obscuring access to other areas of the branched location, the flareable stent graft 10 is placed within the lumen of the branch vessel 4 and is oriented with its flaring portion 20, at the opening, or ostium, 3 of the branch vessel lumen and with the tubular body portion 30 extending distally within the branch lumen beyond the damaged or defective portion.

In FIG. 10, the flareable stent graft 10 is deployed such that the flaring portion 20 engages the ostium 3 of the branch vessel 4. In FIG. 11, the flareable stent graft 10 is placed within the branch lumen and is oriented such that the flaring portion 20 extends through a fenestration 8 of a fenestrated stent graft 7 and the tubular body portion 30 extends distally into the branch lumen beyond the damaged or defective portion. The flareable stent graft 10 is expanded and deployed such that the flaring portion 20 is secured within the fenestration 8 of the stent graft 7 and the tubular body portion 30 secures to the branch lumen 4.

The flaring portion 20 of the flareable stent graft 10 may be riveted to the fenestration 8 of the fenestrated stent graft 7. To rivet the flaring portion 20 of the flareable stent 10, a large diameter compliant balloon catheter (not shown) is delivered within the stent graft 10 so that the balloon is adjacent to the interface between the flaring portion 20 and the body portion 30 of the stent graft 10. The balloon is then sufficiently inflated to flare the flaring portion 20 of the stent graft 10 into the main stent graft 7 to create a union between the main stent graft 7 and the branch stent graft 10. The large diameter compliant balloon is then deflated and removed.

Figure 13:
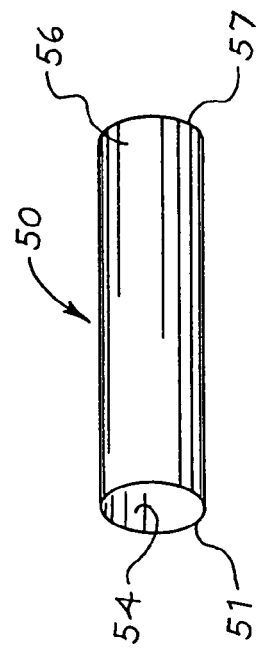
FIGS. 12 and 13 are perspective views of graft member configurations.
Figure 12:
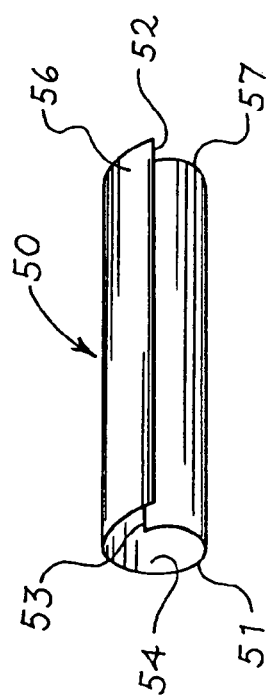

FIGS. 12 and 13 illustrate several configurations of graft members 50. Graft member 50 comprises a graft member interior surface 54, a graft member exterior surface 56, a graft member proximal end 51 and a graft member distal end 57. In one example, graft member 50 is made from one or more layers of material having opposed edges 52, 53 that are formed in a generally circular configuration such that the opposed edges 52, 53 are adjacent to and overlap each other, as shown in FIG. 12. Alternatively, as shown in FIG. 13, the graft member 50 may comprise a tubular configuration.

Although not specifically shown, more than one graft member may be retained between the inner and the outer stents. For example, the inner and outer stents of the flaring portion may retain at least one first graft member and the inner and outer stents forming a body portion may retain at least one second graft member. The multiple graft members may be positioned adjacent to, or spaced apart from each other.

The compressed and deployed configurations of the inner and outer stents may be manipulated by the selection of the materials of construction for the inner and outer stents. For example, inner and outer stents may comprise various shape memory materials exhibiting different shape memory properties. Alternatively, the compressed and deployed configurations of the inner and outer stents may be manipulated by the selection of the stent configuration alone, or in combination with the selection of the materials of construction, for the inner and outer stents.

The stent graft 10 may be assembled with any of the inner and outer stents 40, 60 in the compressed, expanded, or partially deployed configuration. According to one method of manufacture, a graft member 50 is first disposed about the inner stent 40 when the inner stent 40 is in a compressed configuration. If the graft member 50 comprises a layer of material having opposed edges 52, 53, as shown in FIG. 12, then the graft member may be wrapped about inner stent 40 to form a generally circular configuration. The graft member 50 may be wrapped such that the opposed edges 52, 53 are adjacent to and/or overlap one another. The degree of overlap of opposed edges 52, 53 may be greater when the inner stent 40 is in the compressed configuration than when in the deployed configuration. Alternatively, if graft member 50 comprises a tubular configuration as shown in FIG. 13, then the graft member 50 is slid onto inner stent 40. In this example, the tubular graft member may have a diameter that is substantially the same as the diameter of the inner stent 40 in the deployed configuration.

The outer stent 60 then may be placed over the inner stent/graft member combination or the inner stent/graft combination is inserted within the outer stent 60 so that the inner surface of the outer stent 60 is adjacent to the exterior surface of the graft member 50. The outer stent 60 may then be compressed about the graft member 50 and the inner stent 40 such that the graft member 50 is retained between the inner stent 40 and the outer stent 60. Alternatively, the inner stent 40 may be expanded such that the graft member 50 is retained between the inner stent 40 and the outer stent 60.

Figure 14:
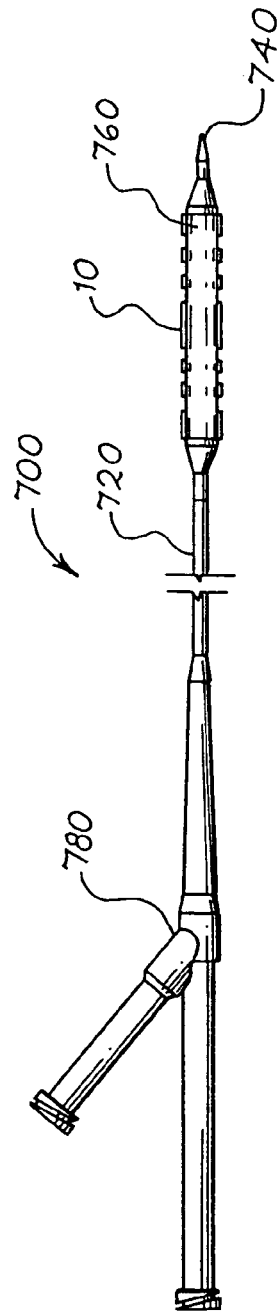
FIG. 14 is a perspective view of a delivery system according to an example of the invention.

FIG. 14 illustrates a delivery system 700 that may be used to deliver and deploy a stent graft. The delivery system 700 includes a catheter 720 having a distal end 740. A connector assembly 780 provides fluid access to the balloon 760, and a wire guide (not illustrated). The balloon 760 may include radiopaque markers (not shown) that are configured to indicate various locations of the flareable stent graft, such as the proximal and distal ends and the flaring portion. The delivery system 700 may be an over-the-wire implantation apparatus or a rapid exchange shuttle system. If an over-the-wire implantation apparatus is used, the delivery apparatus is advanced over a wire guide to a site for deployment.

The flareable stent graft 10 may be disposed on the distal end 740 of the catheter 720, as shown in FIG. 14. The stent graft 10 may have radiopaque markers (not shown) that may be aligned with the radiopaque markers on the catheter 720 and markers on the main vessel stent graft 7 that indicate the fenestration, when a fenestrated stent graft 7 is used. The flareable stent graft 10 surrounds the balloon 760 and is crimped to the balloon 760 in a compressed configuration prior to placement in a body vessel. This positioning allows the balloon 760, upon inflation, to expand the flareable stent graft 10 into its deployed configuration.

A method of deploying a flareable stent graft 10 in a branch vessel is now described. The flareable stent graft 10 is well suited for providing artificial support to a branch lumen in need of such support. The stent graft 10 is delivered and deployed in the branch lumen 4 by inserting the distal end 740 of the catheter 720 into a body vessel, such as the femoral artery, and navigating the distal end 740, and the surrounding flareable stent graft 10 to the branch vessel in need of support. The catheter 720 may be placed over a wire guide (not shown) to facilitate navigation. Optionally, the pre-mounted flareable stent graft 10 and delivery system 700 may be advanced into a guiding catheter or introducer sheath (not shown).

If the flareable stent graft 10 is to be placed within a fenestration 8 of a fenestrated stent graft 7, radiopaque markers (not shown) on the catheter 720 and/or the stent graft 10 may be aligned with corresponding markers (not shown) in the fenestrated stent graft 7 to aid the operator in properly positioning the flareable stent graft 10 through the fenestration 8, so that the flaring portion 20 is adjacent to the fenestration.

Once the flareable stent graft 10 is properly positioned at the repair site, the introducer sheath, if used, is withdrawn to expose the flareable stent graft 10 and the balloon 760 of the delivery system 700. Optimal placement of the flareable stent graft 10 may result in the flaring portion 20 extending within the main body lumen 6.

Next, the balloon 760 is inflated so that it applies pressure to the stent graft 10 and expands it. The body portion 30 of the stent graft 10 expands to engage the branch vessel 4, while the flaring portion 20 expands and flares radially outwardly to engage the ostium 3 of the branch vessel 4, or the fenestration 8 of a fenestrated stent graft 7. A separate balloon catheter may be provided to flare the flaring portion and/or to rivet the flaring portion to the fenestration 8.

Throughout this specification various indications have been given as to preferred and alternative examples of the invention. However, it may be understood that the invention is not limited to any one of these. It is therefore intended that the foregoing detailed description be regarded as illustrative rather than limiting, and that it be understood that it is the appended claims, including all equivalents, that are intended to define the spirit and scope of this invention.

What is claimed is:

1. An endoluminal prosthesis having a compressed configuration and an expanded configuration, the prosthesis comprising:
   a first generally tubular stent;
   a second generally tubular stent disposed radially about the first tubular stent; and
   a generally tubular graft member disposed between the first stent and the second stent;
   where the first stent has a first recoil force and the second stent has a second recoil force such that the combined application of the first and second recoil forces secures the graft member between the first and second stents; and
   where the second stent comprises a flaring portion and a body portion, and where in the compressed configuration, the flaring portion and the body portion lie in the same plane.

2. An endoluminal prosthesis having a compressed configuration and an expanded configuration, the prosthesis comprising:
   a first generally tubular stent;
   a second generally tubular stent disposed radially about the first tubular stent; and
   a generally tubular graft member disposed between the first stent and the second stent;
   where the first stent has a first recoil force and the second stent has a second recoil force such that the combined application of the first and second recoil forces secures the graft member between the first and second stents:
   where one of the first stent and the second stent comprises a flaring portion and a body portion, and where in the compressed configuration, the flaring portion and the body portion lie in the same plane and where in the compressed configuration, the flaring portion of the one of the first and second stent extends longitudinally beyond an end of the other of the second and first stent;
   where the second recoil force is greater than the first recoil force, the first recoil force decreasing the diameter of the first stent by about 0% to about 7% and the second recoil force decreasing the diameter of the second stent by about 4% to about 10%;
   where at least one of the first and second stents comprises a series of interconnected stent rings;

where one of the first stent and the second stent is balloon-expandable and the other of the second and the first stent is self-expanding; and where the first and second stents are made of biocompatible material selected from the group of stainless steel, platinum, gold, titanium, Nitinol, nickel-titanium alloys, MP35N, nickel-cobalt alloys, Cobalt L-605, cobalt-chromium alloys, biocompatible metals, metal-alloys and polymeric materials.

3. A system for repairing a branched vessel having a main lumen and a branch lumen, the system comprising:

a main vessel stent graft having a fenestration and being deployable within the main lumen so that the fenestration is aligned with the branch lumen;

a branch vessel stent graft having a body portion and a flaring portion and being deployable within the branch lumen so that the flaring portion extends at least partially through the fenestration, the branch vessel stent graft comprising:

a first generally tubular stent having a first body portion and a first flaring portion;

a second generally tubular stent having a second body portion, where one of the first and second stent is disposed concentrically about the other of the second and first stent to define an outer stent and an inner stent; and a generally tubular graft member disposed between the first and second body portion;

where the first stent has a first recoil force and the second stent has a second recoil force such that the combined application of the first and second recoil forces secures the graft member between the first and second stents.

4. The system of claim 3 where the second stent has a flaring portion, and where the flaring portion of the first stent is at least partially aligned with the flaring portion of the second stent and the tubular portion of the first stent is at least partially aligned with the tubular portion of the second stent.

5. The system of claim 3 where the recoil force of the outer stent is greater than the recoil force of the inner stent.

6. The prosthesis of claim 5 where the recoil force of the inner stent decreases the diameter of the inner stent by about 0% to about 7% and the recoil force of the outer stent decreases the diameter of the outer stent by about 4% to about 10%.

7. The system of claim 3 where at least one of the first and the second stent comprises a series of stent rings.

8. The system of claim 3;

where the second stent has a flaring portion, and where the flaring portion of the first stent is at least partially aligned with the flaring portion of the second stent and the tubular portion of the first stent is at least partially aligned with the tubular portion of the second stent; and where the recoil force of the outer stent is greater than the recoil force of the inner stent, the recoil force of the inner stent decreasing the diameter of the inner stent by about 0% to about 7% and the recoil force of the outer stent decreasing the diameter of the outer stent by about 4% to about 10%; and where at least one of the first and the second stents comprises a series of stent rings.

* * * * *